United States Patent [19]

Cohen et al.

[11] Patent Number: 4,996,194

[45] Date of Patent: Feb. 26, 1991

[54] PRESSURE TREATED AUTOIMMUNE SPECIFIC T CELL COMPOSITIONS

[75] Inventors: Irun R. Cohen; Meir Shinitzky, both of Rehovot, Israel

[73] Assignee: Yeda Research and Development Co. Ltd., Rehovot, Israel

[21] Appl. No.: 910,876

[22] Filed: Sep. 23, 1986

Related U.S. Application Data

[63] Continuation-in-part of Ser. No. 648,802, Sep. 7, 1984, Pat. No. 4,634,590.

[30] Foreign Application Priority Data

Sep. 11, 1983 [IL] Israel ............................ 69686

[51] Int. Cl.$^5$ .................. A61K 39/39; A61K 41/00; A61K 45/05
[52] U.S. Cl. ................... 514/21; 530/350; 530/359; 530/315; 530/402; 530/403; 530/406; 530/427; 530/806; 435/240.2; 435/240.1; 435/820; 424/88; 514/8; 514/2
[58] Field of Search ........... 435/172.1, 176, 177; 424/101; 514/21; 530/350, 359, 395, 402, 403, 404, 427, 806

[56] References Cited

U.S. PATENT DOCUMENTS

| | | | |
|---|---|---|---|
| 4,046,877 | 9/1977 | White et al. | 424/101 |
| 4,133,804 | 1/1979 | Bach et al. | 424/101 |
| 4,634,590 | 1/1987 | Cohen et al. | 514/21 |
| 4,690,915 | 9/1987 | Rosenberg | 424/101 |

FOREIGN PATENT DOCUMENTS 2146338  4/1985  United Kingdom .

OTHER PUBLICATIONS

Forman, J. Immunol., 118(5):1755-, (1977).
Thomas, J. Immunol., 121(5):1760-, (1978).
Dabrowska et al, Chem Abs, 98: 175125v, (1983).
Gallaher et al, Chem. Abs., 105: 224314e (1986).
Maron et al, J. Immunol., 131(5) (1983), pp. 2316-2321.
Holoshitz et al, J. Immunol., 131(6), 2810-, (1983).
Holoshitz et al, Science, 219, 56-58 (1983).
Lider et al, PNAS (USA), 84, 4577-4580 (Jul. 1987).
Lider et al, Ann. N.Y. Acad. Sci., 475, pp. 267-273 (Jul. 1986).
Sridama et al, J. Clin. End. Met., 54(2), 316 (1982).
Iwatani et al, J. Clin. End. Met., 56(2), 251 (1983).
Ben-Nun et al, "The Rapid Isolation of Clonable Antigen-Specific T Lymphocyte Lines Capable of Mediating Autoimmune Encephalomyelitis", *Eur. J. Immunol.*, 11:195-199 (1981).
Ben-Nun et al, "Spontaneous Remission and Acquired Resistance to Autoimmune Encephalomyelitis (EAE) are Associated with Suppression of T Cell Reactivity: Suppressed EAE Effector T Cells Recovered as T Cell Lines", *J. Immunol.*, 128:1450-1457 (1982).
Ben-Nun et al, "Experimental Autoimmune Encephalomyelitis (EAE), Mediated by T Cell Lines: Process of Selection of Lines and Characterization of the Cells", *J. Immunol.*, 129:303-308 (1982).
Ben-Nun et al, "Experimental Autoimmune Eucephalomelitis (EAE) in Genetically Resistant Rats: PVG Rats Resist Active Induction of EAE but are Susceptible to and Can Generate EAE Effector T Cell Lines", *J. Immunol*, 129:918-919 (1982).

(List continued on next page.)

*Primary Examiner*—Margaret Moskowitz
*Assistant Examiner*—Jeff Kushan
*Attorney, Agent, or Firm*—Browdy and Neimark

[57] ABSTRACT

Composition for the prevention and treatment of autoimmune diseases are provided which comprise as an active ingredient membrane material shed from autoimmune T lymphocytes, or activated T lymphocytes which are treated by a pressure application and releases process. There is also provided processes for obtaining such active materials and for preparing pharmaceutical compositions containing them.

34 Claims, 5 Drawing Sheets

Ben-Nun et al, "Vaccination Against Autoimmune Encephalomyelitis with T-Lymphocyte Line Cells Reactive Against Myelin Basic Protein", *Nature*, 292:60-61 (1981).

Ben-Nun et al, "Vaccination Against Autoimmune Encephalomyelitis (EAE): Attenuated Autoimmune T Lymphocytes Confer Resistance to Induction of Active EAE but not to EAE Mediated by the Intact T Lymphocyte Line", *Eur. J. Immunol,* 11:949-952 (1981).

Muller et al, "Passive Shedding of Erythrocyte Antigens Induced by Membrane Rigidification", *Exp. Cell Research*, 136:53-62 (1981).

Choug, "Pressure Effects on Liposomes, Biological Membranes and Membrane-Bound Proteins", *Diss. Abstr. Int. B*, 43 (9), 2876 (1983).

Zimmerman et al, "The Effects of Hydrostatic Pressure on Cell Membranes", *Chemical Abstracts*, 88:17431f (1978).

MacDonald, "Molecular and Cellular Effects of Hydrostatic Pressure; A Physiologist's View", *Chemical Abstracts*, 95:110223u (1981).

Borochor et al, "Vertical Displacement of Membrane Proteins Mediated by Changes in Microviscosity", *Chemical Abstracts*, 86:53224h (1977).

Shinitzky et al, "Regulation of Tumor Growth by Lipids, Possible Clinical Applications", *Chemical Abstracts*, 98:137302t (1983).

Clark et al, "X-Ray Diffraction Studies of Globular Proteins III, The Action of Formaldehyde on Proteins", *Chemical Abstracts*, 31:3071-3072 (1937).

Fagraeus et al, "The Effect of Colchicine on Circulating Antibodies Antibody-Producing Tissues, and Blood Cells in Rats", *Chemical Abstracts*, 48:3535g (1954).

Jung et al, "Linkage of Formaldehyde to and its Effect on Erythrocytes", *Chemical Abstracts*, 49:6338f (1955).

Schroeder, "Contractile Ring, I. Fine Structure of Dividing Mammalian (Mela) Cells and the Effect of Cytochalasin B", *Chem Abst.*, 75:61744r (1971).

Carter, "Cytochalasins as research tools in cytology", *Chem. Abs.*, 77:29524z (1972).

Shinitzky et al, "Microviscosity Parameters and Protein Mobility in Biological Membranes", *Chem. Abs.*, 84:160894g (1976).

Cohen, "Regulation of Autoimmune Disease Physiological and Therapeutic", *Immunological Review*, 94, 5-22 (1986).

Lider et al, "Anti-Idiotypic Network Induced by T Cell Vaccination Against Experimental Antimmune Encephalomyelitis", *Science*, 239, 181-183, Jan. 8, 1988.

PRESSURE TREATED AUTOIMMUNE SPECIFIC T CELL COMPOSITIONS

This application is a continuation-in-part of U.S. Ser. No. 648,802, filed Sept. 7, 1984, now U.S. Pat. No. 4,634,590 the contents of which are hereby incorporated by reference into the present application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The invention relates to novel preparations and drugs for the treatment and prevention of autoimmune diseases, which are based on immunogenic materials obtained from membranes of certain cells and cell lines of autoimmune lymphocytes or which are based on activated cells which have been treated with a novel pressure treatment, a chemical cross-linking agent, or a cytoskeletal disrupting agent.

The preparations for the prevention of autoimmune diseases include vaccines which comprise membrane proteins obtained from specific autoimmune T cell lines containing certain T cell receptors or pressure-treated activated T cells. The invention further provides processes for the preparation of such active cell membrane materials and for the treatment of activated cells, and to pharmaceutical compositions which contain either the cell membrane materials or the activated cells as their active ingredient.

The etiological agents of autoimmune diseases are endogenous lymphocytes which attack normal constituents of the individual. The inventors have been engaged in growing as long term cell lines specific autoimmune T lymphocytes which produce a number of experimental autoimmune diseases (1–9). The thus obtained comparatively pure cultures of autoimmune cells have facilitated investigation of pathogenesis, uncovered the carrier state of autoimmunity and provided means for vaccination against, and treating, autoimmunity (5–9).

SUMMARY OF THE INVENTION

The present invention relates to novel preparations for use in the prevention and treatment of autoimmune diseases, said preparations having as their active ingredient certain membrane materials of specific autoimmune T lymphocytes or such pressure treated-activated T lymphocyte cells. The invention further relates to a process for obtaining such materials from such lymphocytes, to the pressure treatment of such lymphocytes and for the preparation of vaccines and pharmaceutical preparation containing same. Other and further features of the invention will become apparent hereinafter.

Autoimmune diseases share the common feature of being caused by the immune system attacking an individual's own tissues. At the seat of all autoimmune diseases are the autoimmune lymphocytes which specifically recognize the individual's particular target antigens. Amongst autoimmune diseases there may be mentioned rheumatoid arthritis, multiple sclerosis, some forms of diabetes mellitus, thyroidrtis, and myasthenia gravis. Hithereto there has not existed any specific form of therapy against these diseases.

It has been found possible to grow as long term cell lines T lymphocytes responsible for causing autoimmune diseases in laboratory animals. Amongst such diseases there may be mentioned encephalomyelitis, arthritis and thyroiditis. Such cells were found to be effective agents for vaccination against such specific autoimmune diseases: such lymphocytes were attenuated and injected so that they would not cause the autoimmune diseases. It was found that such vaccinations were quite effective in rendering such animals immune to, or less sensitive (the disease was much less severe) to such diseases. Furthermore, it was shown that when such animals were inoculated with such cells, this constituted a quite effective treatment of the disease.

According to the present invention there are provided pharmaceutical preparations which contain as their active ingredient membrane material from specific autoimmune T cells which contain certain T cell receptors. The invention also provides a novel process for the production and isolation of such membrane material which comprises exposing such T lymphocytes to a high hydrostatic pressure and gradually releasing the pressure, thus resulting in an effective shedding of membrane material which retains a high degree of biological activity. An alternative is the pressure treatment of such T cells by subjecting them to hydrostatic pressure, and releasing such pressure in a gradual manner.

Typical conditions for the shedding of the active material are pressures of the order of 500 to 1500 atmospheres, the build up of pressure being gradually over 5 minutes, maintaining such pressure at the upper level for about 10 to 45 minutes, and gradually releasing the pressure over 5 to 15 minutes.

Pressure treatment of activated T cells is attained by subjecting such cells to a build up of pressure during about 5 minutes, going up from 500 to about 1300 atmospheres, maintaining the pressure for about 5 minutes and gradually releasing the pressure during about 5 minutes.

Practically no shedding takes place. Both the shed material as well as the pressure-treated, activated cells may be used as active ingredients in the vaccines of the present invention: the cells retain their full viability.

The materials thus obtained comprise about $10^7$ to $10^8$ activated cells or the material from an equal number of cells. For vaccination of humans there is used a quantity of the order of about 0.01 mg to about 3 mg of such materials (shed protein or pressure-treated, activated T cells), vaccination being given 3–4 times with an interval of about 2 weeks between applications.

Such immunizations are effective for the prevention and treatment of certain autoimmune diseases.

The pressure treatment comprises suspending lymphocytes in a suitable buffer, inserting the suspension into a pressure vessel devoid of any gaseous medium and applying pressure, e.g. with a French press, as set out above.

The resulting cell suspension is subjected to centrifugation at about 1500 rpm and the supernatant is subjected to ultracentrifugation at about 100,000 g for about 1 hr to precipitate he membrane fragments. When pressure-treated, activated T cells are prepared, these are collected by centrifugation.

According to a further embodiment of the invention, purified membrane proteins from T lymphocyte cells useful for preventing or treating a specific autoimmune disease may be produced by subjecting such cells to a treatment which results in the formation of stable aggregates of cell membrane glycoproteins. It is believed that such aggregates include T cell receptors, probably in combination with one or more unidentified molecules which appear after activation of the T cells by treatment with a mitogen or an antigen.

Figure 3:
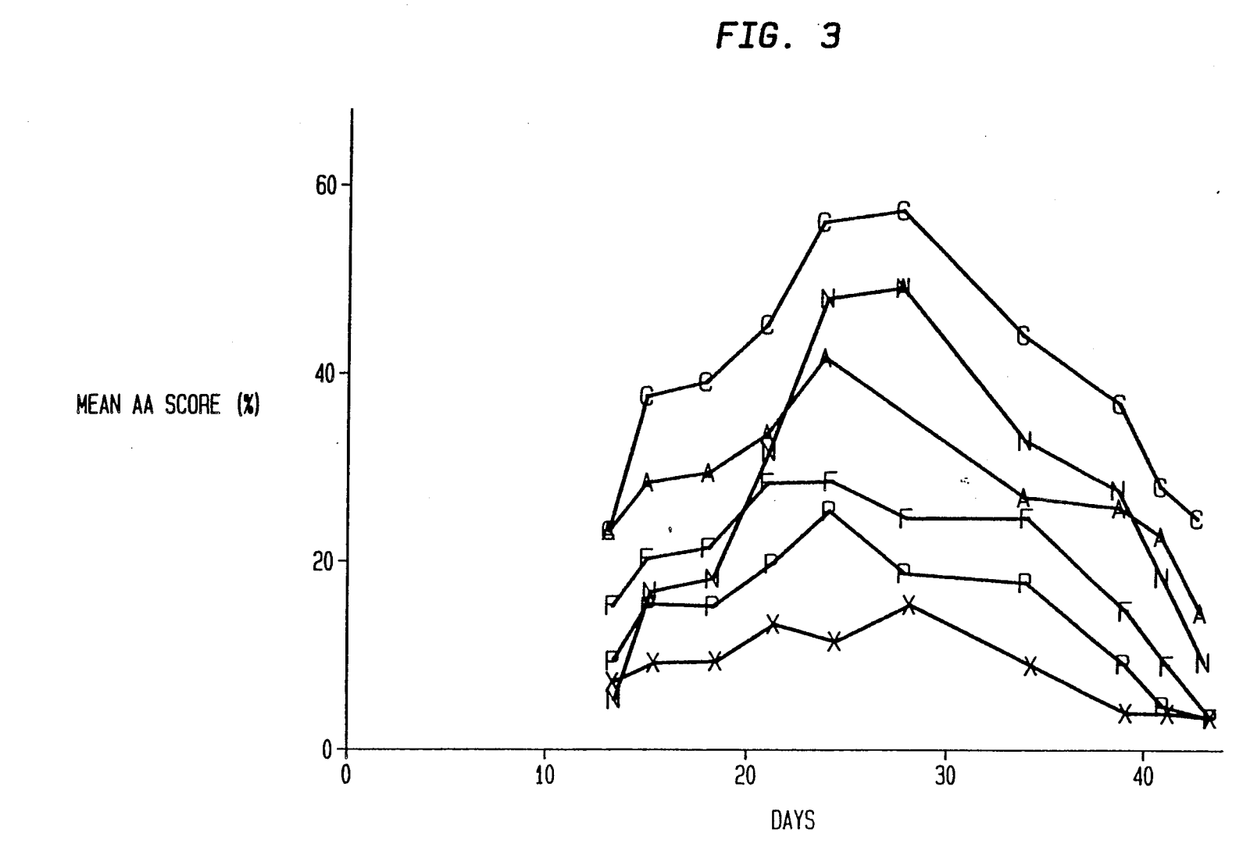
Figure 4:
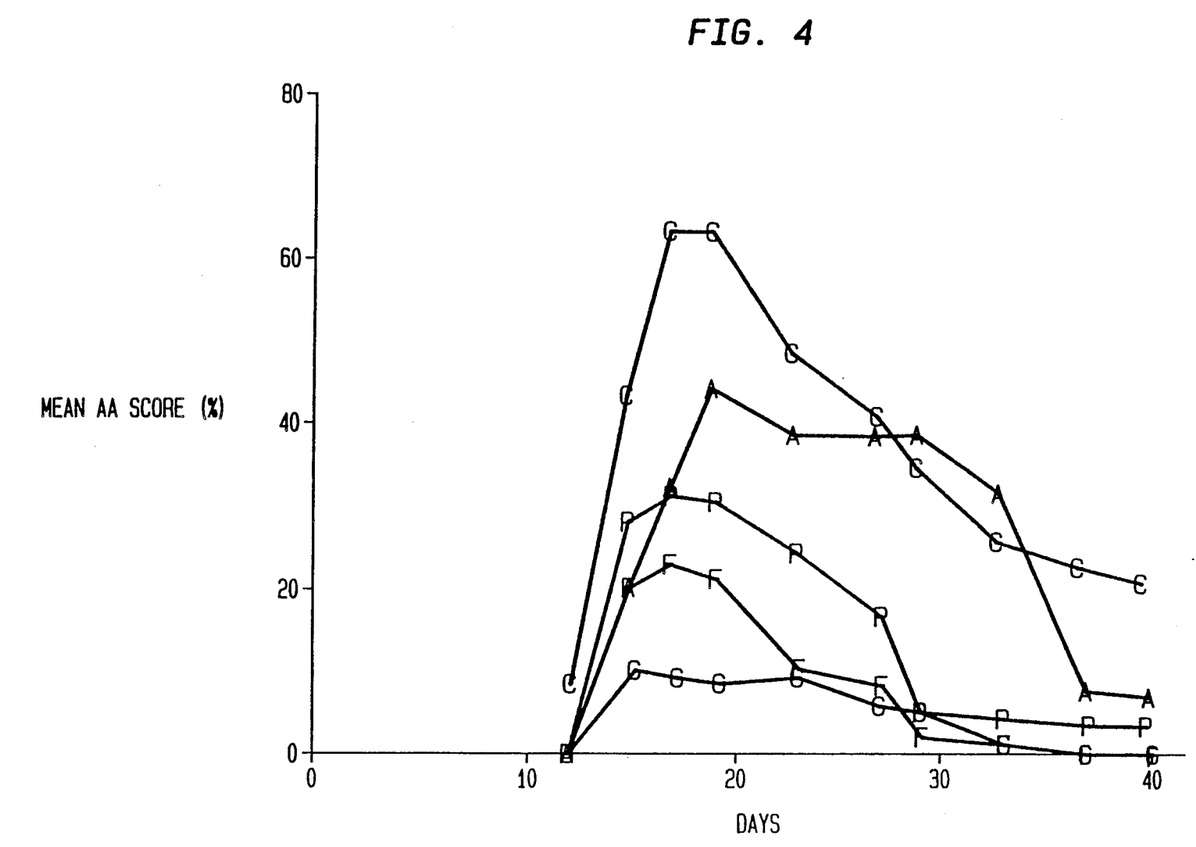
Figure 5:
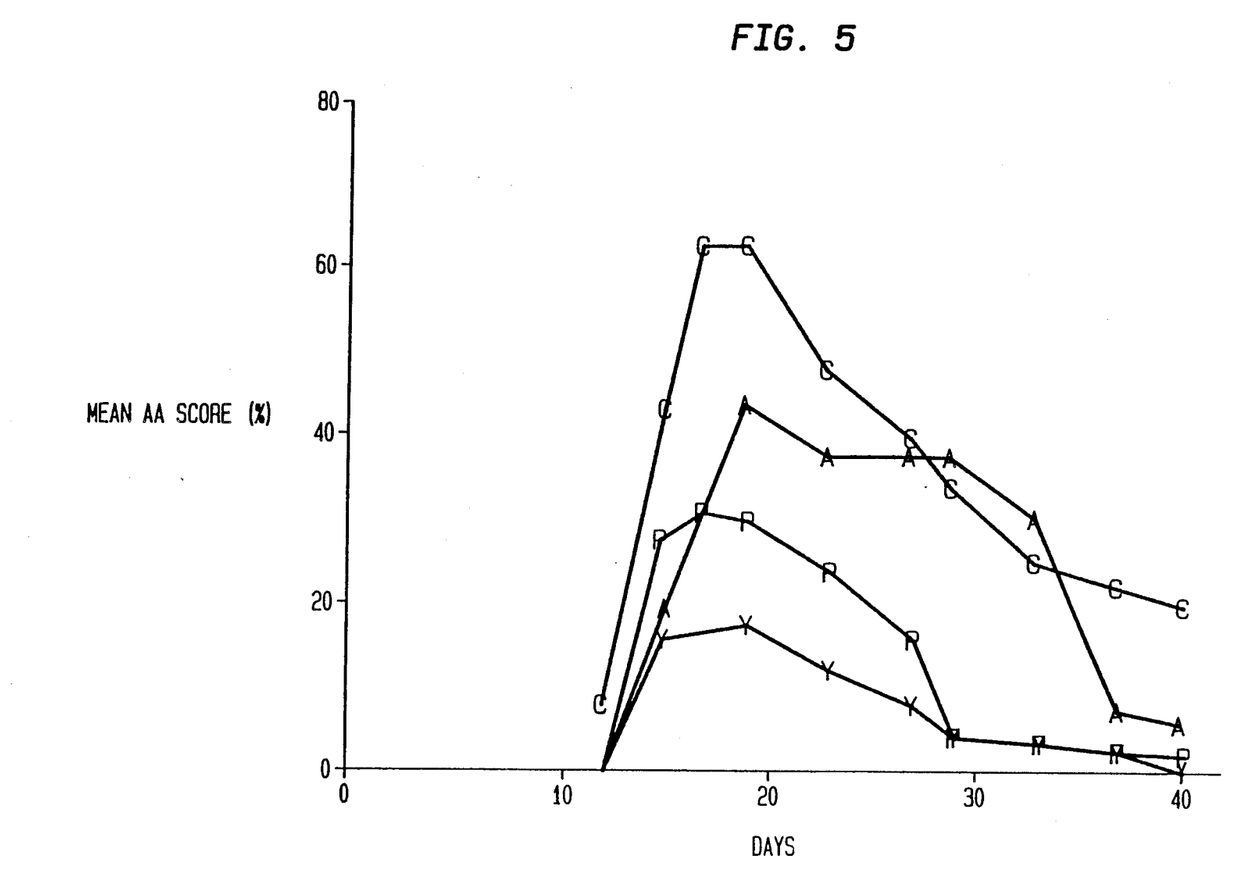
FIG. 5 Inhibition of adjuvant arthritis by a T lymphocyte vaccine prepared with cytoskeletal disruptors. The experiment was performed as described in the description of FIGS. 3. Y signifies A2b cells that had been treated with colchicine (10 micromolar) plus cytochalsin (0.5 micrograms/ml) for 15 min before vaccination.

Instead of subjecting the T cells to a pressure treatment, they may be subjected to a treatment with a suitable chemical cross-linking agent, such as formaldehyde, glutaraldehyde or the like (see FIGS. 3, 4 and 5). Such treatment is also of value when applied prior or subsequent to the pressure treatment.

According to yet a further embodiment of the invention, such T cells may be subjected to a treatment adapted to disrupt the cytoskeleton of said T lymphocytes. Conventional cytoskeletal disrupting agents, such as cytochalsin (0.5 micrograms/ml) or colchicine (10 micromolar) may be used.

When chemical cross-linking agents of the type defined above are used, such treatment makes possible the use of isolated cell membranes which are prevented from disintegration after disruption of the cells. While pressure treated cells lose some of their vaccination effectiveness after lysing of the cells, cells subjected to chemical cross-linking do not lose such effectiveness.

According to the above, a variety of treatments of T lymphocyte cells, or a combination of such treatments may be used in order to obtain effective means for the prevention and treatment of certain diseases.

The cross-linking of membrane proteins is advantageously effected by treatment with an agent like formaldehyde or glutaraldehyde (about 0.3 to 1 percent for a period of time of about 15 minutes).

The disruption of the cytoskeleton may be effected by treatment with an agent such as a combination of cytochalsin (about 0.5 micrograms/ml) and colchicine (about 10 micromolar).

After cross-linking, the fixed cell membranes may be obtained by suspending the cells in a suitable hypotonic solution, homogenizing and isolating them using a discontinuous sucrose gradient, followed by dialysis of the separated membranes against phosphate buffered saline (PBS).

The following experiments illustrate some of the results obtained by treating T lymphocyte cells according to the methods described above. The details of the experiments are as follows:

BRIEF DESCRIPTION OF THE FIGURES

FIG. 1. Treatment of ongoing arthritis by line cells. Active adjuvant arthritis was induced in 20 Lewis rats by inoculation of CFA. Five days after the onset of clinical arthritis (arrow, day 16), one group of 10 rats was treated by a single intravenous inoculation of activated anti-Tb line cells (closed circles). A second group of 10 rats were treated with an irrelevant control line (open circles). The mean arthritis score was determined as described in (5).

FIG. 2 Alleviation of EAE by administration of membrane fraction. Rats were inoculated twice at a one week interval with membrane fractions of Z1a line cells (0.5 micrograms obtained by pressure method) and two weeks later challenged with an encephalogenic dose of EAE. The clinical score of the test rats is indicated by the open circles and the control rats by the closed circles. Clinical score: 1—mild; 2—moderate; 3—severe.

FIG. 3 Inhibition of adjuvant arthritis by T lymphocyte vaccines. Adjuvant arthritis was induced in groups of 10 Lewis rats by immunizing them intradermally at the base of the tail with *Mycobacterium tuberculosis* (MT) H37RA (1 gm) in oil. The severity of disease was graded on a scale of 0 to 100% based on swelling, redness, deformity and lack of function of the paws. The groups were as follows:

C—control, no vaccination.

A—vaccinated before induction of arthritis with 3 weekly injections subcutaneously with $20 \times 10^6$ cells of the clone A2b, that had been activated by incubation for 3 days with the T cell mitogen Concanavalin A (1.5 micrograms/ml).

N—vaccinated with A2b cells that were not activated but were treated with formaldehyde (0.3% for 15 min).

F—vaccinated with activated A2b cells that were treated with formaldehyde.

P—vaccinated with activated A2b cells that were treated with hydrostatic pressure (1250 bars, 15 min).

X—vaccinated with activated A2b cells that were first treated with pressure and then with formaldehyde.

FIG. 4 Inhibition of adjuvant arthritis by T lymphocyte vaccines. The experiment was performed as described in the description of FIG. 3 and the groups have the same labels except that F here signifies treatment of the A2b cells with formaldehyde (0.3%) after treatment with pressure (1500 bars) and G signifies treatment of the A2b cells with glutaraldehyde (0.3%) after treatment with pressure.

DETAILED DESCRIPTION OF THE INVENTION

The present invention provides a pressure-treated, activated T lymphocyte cell useful for preventing or treating a specific autoimmune disease. The T lymphocyte cells of the present invention may be derived from an established cell line or may be taken from the circulatory or lymphatic systems of a subject, e.g. a mouse, a rat or a human. Additionally, the T lymphocyte cells may be taken directly from a patient who is to be treated for a specific autoimmune disease. Within this application, "activated T lymphocyte cell" means a T lymphocyte cell which has been exposed to a specific antigen or mitogen capable of inducing an immune response by the T lymphocyte cell. Suitable mitogens are known in the art and include concanavalin A, phytohemagglutinin, and pokeweed mitogen. The pressure-treated, activated T lymphocyte cells of the present invention may be useful for treating multiple sclerosis, thyroiditis, diabetes type I, ankylosing spondylitis, rheumatoid arthritis, or myasthenia gravis.

Additionally, the pressure-treated, activated T lymphocyte cells of the present invention may additionally be treated with a chemical cross-linking agent. Suitable chemical cross-linking agents are known in the art and include, but are not limited to, formaldehyde and glutaraldehyde. In one embodiment of the invention, the pressure-treated, activated T lymphocyte cells are treated with the chemical cross-linking agent after being treated with hydrostatic pressure. In another embodiment of the invention, the pressure-treated, activated T lymphocyte cells are treated with the chemical cross-linking agent prior to being treated with hydrostatic pressure.

Moreover, the pressure-treated, activated T lymphocyte cells of the present invention may be treated with a disrupting agent. Within this application, a disrupting agent means an agent capable of causing the cell's cytoskeleton to dissociate. Such disrupting agents include the chemicals cytochalasin and colchicine, however other disrupting agents are known in the art and may also be used. These disrupting agents may be used individually or in combination with each other. In one embodiment of the invention, the pressure-treated, activated T lymphocyte cells are treated with the disrupting agent after being treated with pressure. In another embodiment of the invention, the pressure-treated, activated T lymphocyte cells are treated with the disrupting agent prior to being treated with pressure. In yet a further embodiment of the invention, the pressure-treated, activated T lymphocytes are treated with both a disrupting agent and a chemical cross-linking agent.

The invention also provides a chemical cross-linking agent-treated, activated T lymphocyte cell useful for preventing or treating a specific autoimmune disease. The autoimmune disease may be multiple sclerosis, thyroiditis, diabetes type I, ankylosing spondylitis, rheumatoid arthritis, or myasthenia gravis.

Further provided are disrupting agent-treated, activated T lymphocyte cells useful for preventing or treating a specific autoimmune disease. The disrupting agent-treated, activated T lymphocyte cells of the present invention may be useful for treating multiple sclerosis, thyroiditis, diabetes type I, ankylosing spondylitis, rheumatoid arthritis, or myasthenia gravis.

Furthermore, the disrupting agent-treated, activated T lymphocyte cells of the present invention may additionally be treated with a chemical cross-linking agent or with hydrostatic pressure.

Further provided is a method for producing pressure-treated, activated T lymphocytes useful for preventing or treating a specific autoimmune disease. This method comprises initially suspending activated T lymphocyte cells specific for the autoimmune disease in a buffer. The suspended cells are then subjected to a suitable hydrostatic pressure for an appropriate period of time. Thereafter, the pressure on the suspended cells is released at an appropriate rate so as to produce pressure-treated, activated T lymphocyte cells without substantial loss of membrane proteins from the cells. In one embodiment of the invention, the suitable pressure is from 500 to about 1500 atmospheres. In another embodiment of the invention, prior to subjecting the suspended cells to a suitable hydrostatic pressure, the suspended cells are treated with a chemical cross-linking agent. In a further embodiment of the invention, the T lymphocyte cells are treated with a disrupting agent in addition to the chemical cross-linking agent. In still another embodiment of the invention, the suspended cells are treated with a chemical cross-linking agent after having been depressurized. In yet a further embodiment of the invention, the T lymphocyte cells are additionally treated with a disrupting agent. In still a further embodiment of the invention, prior to subjecting the suspended cells to a suitable hydrostatic pressure, the suspended cells are treated with a disrupting agent.

Moreover, in another embodiment of the invention, the suspended cells are treated with a disrupting agent after having been depressurized.

Also provided is a method for producing chemical cross-linking agent-treated, activated T lymphocytes useful for preventing or treating a specific autoimmune disease. This method comprises suspending activated T lymphocyte cells specific for the autoimmune disease in a buffer and treating the suspended cells with a chemical cross-linking agent.

The present invention also provides a method for producing disrupting agent-treated, activated T lymphocyte cells useful for preventing or treating a specific autoimmune disease. The method comprises suspending activated T lymphocyte cells specific for the autoimmune disease in a buffer and treating the suspended cells with a disrupting agent so as to produce activated T lymphocyte cells having dissociated cytoskeletons. Additionally, the resulting activated T lymphocyte cells having dissociated cytoskeletons may be treated with a chemical cross-linking agent.

The present invention also provides a composition for preventing or treating a specific autoimmune disease. This composition comprises pressure-treated, activated T lymphocyte cells of the present invention and a pharmaceutically acceptable carrier. Pharmaceutically acceptably carriers are known in the art and include, but are not limited to, 0.01–0.1M, preferably 0.05M, phosphate buffer, or 0.8% saline. Another composition for preventing or treating a specific autoimmune disease is also provided. This composition comprises chemical cross-linking agent-treated, activated T lymphocyte cells of the present invention and a pharmaceutically acceptable carrier. Yet a further composition for preventing or treating a specific autoimmune disease is provided by the present invention. This composition comprises disrupting agent-treated, activated T lymphocyte cells of the present invention and a pharmaceutically acceptable carrier.

Also provided are methods for preventing or treating a specific autoimmune disease in a subject. These methods comprise administering to a subject by an appropriate route, an effective amount of a composition of the present invention. Appropriate routes of administration include oral, intranasal or transdermal administration, as well as intramuscular, intravenous, intradermal, subcutaneous and intraperitoneal injections.

The present invention further provides a method for recovering purified membrane proteins from activated T lymphocyte cells useful for preventing or treating a specific autoimmune disease. This method comprises initially suspending activated T lymphocyte cells specific for the autoimmune disease in a buffer. The suspended cells are subjected to a suitable hydrostatic pressure for an appropriate period of time so as to cause membrane proteins to be shed. Thereafter, the pressure on the suspended cells is released at an appropriate rate. The depressurized suspension is centrifuged containing the membrane proteins. This supernatant may be ultracentrifuged so as to recover the purified membrane proteins. In one embodiment of the invention, the suspended cells, prior to being subjected to the suitable hydrostatic pressure, are treated with a chemical cross-linking agent. In another embodiment of the invention, the suspended cells, subsequent to being depressurized, are treated with a chemical cross-linking agent. In a further embodiment of the invention, the suspended cells, prior to being subjected to a suitable hydrostatic pressure, are treated with a disrupting agent. In yet a further embodiment of the invention, the depressurized cells may be treated with a disrupting agent. In still another embodiment of the invention, the suitable hydrostatic pressure is from 500 to about 1500 atmospheres. In yet another embodiment of the invention, prior to ultracentrifuging the supernatant, the shed membrane proteins are treated with a chemical cross-linking agent.

The various cells, treatments and proteins provided by the present invention will be better understood by reference to the following experiments and examples which are provided for purposes of illustration and are not to be construed as in any way limiting the scope of the present invention, which is defined by the claims appended hereto.

Materials and Methods

Rats

Inbred Lewis rats were obtained from the Animal Breeding Center of The Weizmann Institute of Science. Rats were used at 2–3 months of age and were matched for age and sex in each experiment.

Antigens

Heat-killed M. tuberculosis $H_{37Ra}$ was purchased from Difco Laboratories (Detroit, MI). Purified protein derivative (PPD) of mycobacterium was purchased from Staten Serum Institute (Copenhagen, Denmark) and concanavalin A (Con A) from Bio-Yeda (Rehovot, Israel). Purified rat type II collagen was kindly donated by Dr. E. J. Miller of the University of Alabama Medical Center, Birmingham. Rat type I collagen was prepared from rat tail tendons and donated by Dr. D. Duskin of the Department of Biophysics of the Weizmann Institute (16).

Culture medium

All cell cultures used Dulbecco's modified Eagle's medium (Grand island Biological Co., (GIBCO), Grand Island, New York). Media used for proliferation assays, for activation, and for cloning (proliferation medium) was supplemented with 1 mM glutamine (Bio-Lab, Jerusalem, Israel), 2-mercaptoethanol ($5 \times 10^{-3}$M), gentamycin (40 micrograms/ml), and 1% fresh autologous rat serum. The medium used to maintain the propagated cell lines and clones in long-term culture (propagation medium) was the proliferation medium supplemented with 15% (vol/vol) of supernatant of ConA-activated lymphocytes as a source of T cell growth factor (3), 10% horse serum (GIBCO), 1 mM sodium pyruvate, and nonessential amino acids (Bio-Lab).

Introduction of active adjuvant arthritis (AA)

To induce active AA, rats were inoculated intradermally at the base of the tail with 0.1 ml of complete Freund's adjuvant (CFA) containing 10 mg/ml MT in incomplete Freund's adjuvant (Difco Laboratories). The system described in (17) was used to assess severity of arthritis. Each paw was graded from 0 to 4 based on erythema, swelling, and deformity of the joint. The highest score achievable was 16. The clinical diagnosis of AA was confirmed by histologic examination of the joints of selected rats as in (18).

Maintenance and clonino of line A2

Line A2 reactive to MT was isolated from rats immunized with CFA. On day 9 the draining lymph nodes were removed, and a T cell line reactive to MT was generated and maintained as described (19). The limiting dilution technique was employed to clone A2. The line cells were activated in vitro by incubating them with MT in the presence of accessory cells, as described below, for 3 days. On the third day, the lymphoblasts were transferred into propagation medium or another 7 day period. On the 10th day, the cells were collected, washed, counted three times, and vigorously mixed. Cells were seeded at 0.1 cells/well in the presence of irradiated (1,500 rad) thymus cells ($2 \times 10^7$/ml) and MT (10 micrograms/ml) into 96-well microtiter plates in 100 microliters of proliferation medium per well.

Wells were checked for cell growth from the 6th to the 14th day after cloning. Plating efficiency was 60%. Cloned cells were expanded in propagation medium in 200 microliter wells and then in 2-, 6-, and finally, 10-ml plates at a concentration of $2-4 \times 10^5$ cells/ml. Cultures were transferred every 3–4 days. Once every 2–4 weeks, the lines cells were reactivated by incubation with MT and accessory cells for 3 days (see below), and then transferred back into propagation medium. Cloned subline A2b was propagated in this manner for 6 weeks before its proliferative response to antigens or its ability to mediate AA or induce resistance was studied.

Activation of line cells

Cells ($2 \times 10^5$/ml) of line A2 or subline A2b were activated by incubation for 3 days with 10 micrograms/ml of MT or 2.5 micrograms/ml of Con A in the presence of syngeneic irradiated (1,500 rad) thymus cells ($15 \times 10^6$/ml) as accessory cells in the proliferation medium. After 3 days the lymphoblasts were collected, washed twice in phosphate-buffered saline (PBS), and were either transferred into propagation medium or used for in vivo or in vitro studies. By this time most of the irradiated thymus cells had died and disintegrated.

Cell modifications

A. Hydrostatic pressure

For pressure application on small volumes (2ml), the cell suspension was placed in a plastic capped tube and sample buffer was added to the top. After sealing, a short 22G needle was inserted through the cap to act as a vent for pressure equilibration. Air bubbles were avoided. The tube was placed in the cavity of a 45 ml pressure bomb (French Press Cell, Aminco). For larger sample volumes the cell suspensions were added directly into the cavity of the pressure bomb.

Hydrostatic pressure was gradually applied at a rate of 250 bar min$^{-1}$, maintained at the desired pressure and thereafter slowly released. The cells were collected and washed twice in PBS.

B. Cross-linking of membrane proteins

Cells were fixed by formaldehyde or glutaraldehyde (0.3–1%) for 15 min. $10^6$–$10^8$ cells are suspended in 2.5 ml PBS. The same volume of a double concentrated solution of cross-linking agent in PBS was added to the cell suspensions at room temperature, after which cells were washed six times in PBS.

Cytoskeletal disruption

The process was performed by the method described in "Cross-linking of membrane proteins", but a combination of cytochalasin (0.5 micrograms/ml) plus colchicine (10 micromolar), was used in place of the cross-linking agent.

D. Membrane preparation

Fixed cell membranes were obtained by suspending cells in PBS hypotonic solution (⅓ physiological osmolarity + PMSF (10-5M) + azide (0.02%)) for 15 min., 4° C. in 5 ml vol., then homogenized in a polytron homogenizer (2.5 min. at intervals of 30 sec., speed 6.5 units, at 4° C.). The membranes were isolated using a discontinuous sucrose gradient (41% sucrose, 96,000 g, 2 h, Rotter SW28, 4° C.). Separated membranes were dialyzed against PBS (2 hours, 4° C.), and measured by Bradford analysis. The yield of proteins achieved by using this method was 1.5-2 mg per $3 \times 10^8$ cells.

EXPERIMENTAL MODELS

Special in vitro lines of autoimmune T cells were developed (1-9). Table 1 summarizes three experimental autoimmune diseases associated with these lines of T lymphocytes. Experimental autoimmune encephalomyelitis (EAE), can be induced actively in genetically susceptible strains of rats by immunizing them to the basic protein of myelin (BP) (10). EAE is usually manifested as an acute disease characterized by paralysis and cellular infiltration in the white matter of the central nervous system. Untreated rats usually recover spontaneously from acute EAE after 2 or 3 days and are found to be resistant to further attempts to induce active EAE (2). Chronic or relapsing EAE can also be induced under certain conditions and such disease is similar in many respects to multiple sclerosis in man.

Experimental autoimmune thyroiditis (EAT) can be induced in H-2 genetically susceptible mice by immunizing thyroglobulin (Tg) in adjuvant (11). EAT is expressed as chronic inflammation of the thyroid gland. Strains of mice resistant to the lesion of EAT may yet produce high titers of Tg autoantibodies. EAT appears to be a model of autoimmune thyroiditis (Hashimoto's thyroiditis) that is not uncommon in humans.

Adjuvant arthritis (AA) differs from EAE and EAT in that it is induced in rats by immunizing them not to a defined self-antigen but to *Mycobacterium tuberculosis* organisms (Tb) in complete Freund's adjuvant (CFA) (12). About two weeks after inoculation, genetically susceptible rats develop a subacute polyarthritis with features reminiscent of some of those seen in rheumatoid arthritis in humans. It has been suggested that collagen type II might be the target self-antigen in AA, as arthritis may be induced by immunization to this antigen (13). However, recent evidence indicates that AA and collagen II arthritis may be separate entities (14, 15).

Table I also illustrates that similar autoimmune lesions may be induced by inoculation of antigen-specific line cells. The details of raising and maintaining the line cells and producing the diseases have been published (1-5). The basis of the method is to prime animals with the antigen of choice and select the specifically reactive cells by culture with the selecting antigen together with irradiated syngeneic accessory cells. The antigen-presenting accessory cells must by syngeneic, at least in part of the major histocompatibility complex (MHC), to trigger the proliferative response of line cells (3, 4). The selected line cells are then carried in culture with conditioned medium in the absence of antigen or accessory cells. Stable lines capable of mediating autoimmune diseases have all been found to be positive for general T cell markers (Thy 1 in mice or W3/13) and for the markers of delayed type hypersensitivity/helper cells (Lyt-1 or W3/25) with a few or no cells positive for the Lyt-2 or $O \times 8$ mark of cytotoxic/suppressor cells. None of the line cells are positive for Ig markers. To mediate disease the T lymphocyte line must be activated by incubation with a specific antigen or T cell mitogen before inoculation into recipient animals. A single inoculation of as few as $10^4$–$10^5$ anti-BP or anti-Tg cells can lead to the clinical and pathological signs of marked EAE and EAT in a relatively short time. Production of AA requires the use of greater numbers of line cells ($10^7$) and relatively heavy irradiation of the recipient rate (750 R). Recipients must be syngeneic with the line cells at part of the MHC for disease to occur. The characteristic autoimmune lesions are accompanied by immunologically specific accumulation of line cells in the target organ. No evidence indicating a role for autoantibodies in disease produced by the T lymphocyte line cells is evident.

We have also succeeded in producing encephalomyelitis or arthritis cloned cells; the anti-BP clones have been somewhat less virulent than their parent lines while an anti-Tb clone has been isolated that is much more virulent than its parent.

Vaccination against autoimmune disease

The use of line cells as specific vaccines to induce resistance to autoimmune disease is summarized in Table II. Anti-BP line cells subjected to irradiation or treated with mitomycen C were no longer capable of producing EAE. However, a single intravenous inoculation of such attenuated line cells led to resistance in about 65% of rats induced actively by immunization with BP/CFA. In early experiments the rats were still susceptible to EAE produced by passive transfer of anti-BP line cells, suggesting that the mechanism of resistance might be less effective against preformed effector cells than against differentiating cells (7). However, we have recently observed that it is possible to prevent EAE due to positive transfer of line cells as well as active EAE using pressure-treated cells (20). In contrast, a single intravenous inoculation of attenuated anti-Tg line cells was found not only to completely inhibit active EAT induced by Tg/CFA, but also to prevent EAT mediated by inoculation of activated anti-Tg line cells. Thus, in principle, resistance to autoimmune disease is not limited to the early phases of differentiation but can include the effector phase of disease. See Table V for results of vaccination experiments performed with pressure, cross-linking agent or disrupting-agent treated T lymphocytes. Furthermore, see FIGS. 3-5 for results of vaccination experiments involving T lymphocytes modified by various methods disclosed by the present invention.

Therapy with membrane proteins

Autoimmune line cells were found to be effective as agents to prevent and treat experimental autoimmunity. This approach may help in the management of clinical autoimmune diseases, illnesses for which there exists no specific mode of therapy. Although the clinical emphasis must be on treatment rather than on prevention, it is possible that in practice this distinction will not be critical. Autoimmune diseases of serious concern are often progressive or relapsing and prevention of the differentiation of fresh waves of autoimmune lymphocytes may, by itself, constitute effective therapy.

Figure 1:
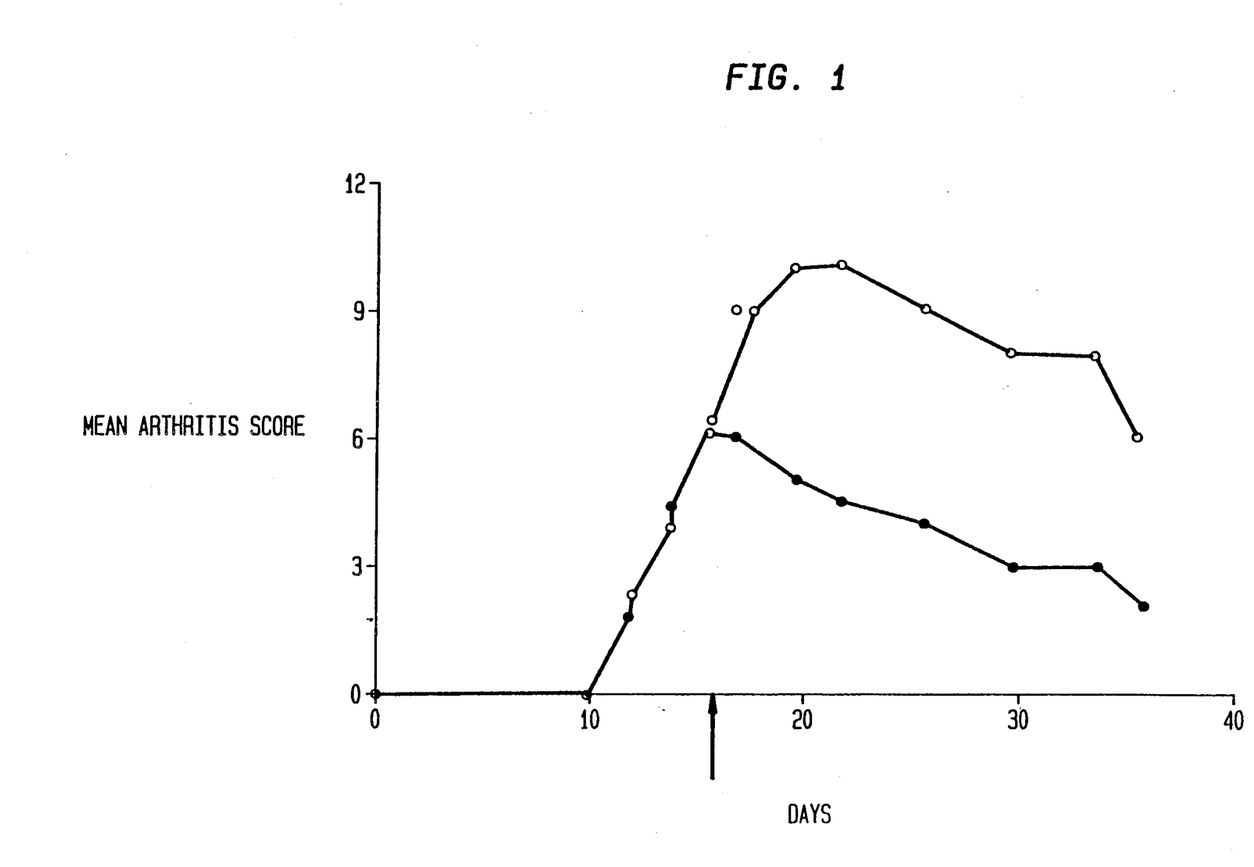

FIG. 1. illustrates alleviation of AA by a single inoculation of line cells. In this experiment groups of rats suffering from actively induced AA were treated with specific anti-Tb line cells or with control line cells. The rats treated with the specific line cells had less severe disease and a hastened remission.

Another consideration is the identification and availability of self-antigens to which the autoimmune lymphocyte lines should be selected In many conditions the self-antigens are unknown or may be in very limited supply. Nevertheless, the AA model suggests that it ought to be possible to raise relevant cell lines using mixtures of poorly defined antigens obtained even from foreign sources. Why or how specifically virulent autoimmune cells should emerge under such conditions is puzzling, but a fact. However, it is not necessary to raise lines or clones of T lymphocytes to obtain effective vaccines Lymph node cells taken directly from rats or mice with AA, EAE, or EAT can be activated with a specific antigen or a T lymphocyte mitogen and treated with pressure, cross-linking agents, or disrupting-agents, and the cells used to obtain the results described in Tables 4, 5 and 6.

It may be advantageous to effect therapy with subcellular material from line cells or with cells of augmented antigenicity and it has been found that membrane proteins may be used effectively. Membrane proteins of line cells were prepared by a novel method which was previously applied for isolation of blood group antigens from human erythrocytes. The method is based on the hypothesis that the equilibrium position of membrane proteins is displaced towards the aqueous domain upon rigidization of the membrane lipid bilayer, and at extreme lipid viscosities proteins are shed. In principle, each integral membrane protein has a defined threshold of lipid viscosity where it is shed from the membrane.

The most efficient manner of hyper-rigidization of membranes is by the application of hydrostatic pressure (500 to 1500 atm) which can be augmented by pretreatment with cholesterol. Cells, in general, survive such treatment and the material which is shed can be fractionated according to size by centrifugation. Material which remains in the supernatant after centrifugation at 100,000 g for 1 hour can be considered as isolated proteins or small aggregates thereof. The precipitate of this centrifugation consists of membrane fragments and large protein aggregates. The soluble membrane proteins retain in general their activity, in contrast to membrane proteins isolated by the conventional use of detergents.

The capacity of immunization against autoimmune diseases was found in the following fractions: (a) pressurized activated cells (presumably due to lateral rearrangement and vertical displacement of the specific antigen receptors; (b) the shed soluble proteins; and (c) the membrane fragments.

Table III shows that membrane fractions isolated by the pressure method were immunologically specific in inhibiting the reaction of autoimmune line cells to their particular antigen. For example, the membrane fraction obtained from the Z1a anti-BP line inhibited the response of intact Z1a line cells to BP; it did not inhibit the response of arthritis-producing A2 line cells to their antigen. Conversely, the membrane fraction obtained from arthritis producing A2 cells inhibited the response of intact A2 line cells, but not of Z1a line cells. These results indicate that the membranes contain biologically active receptors specific for self antigens.

Figure 2:
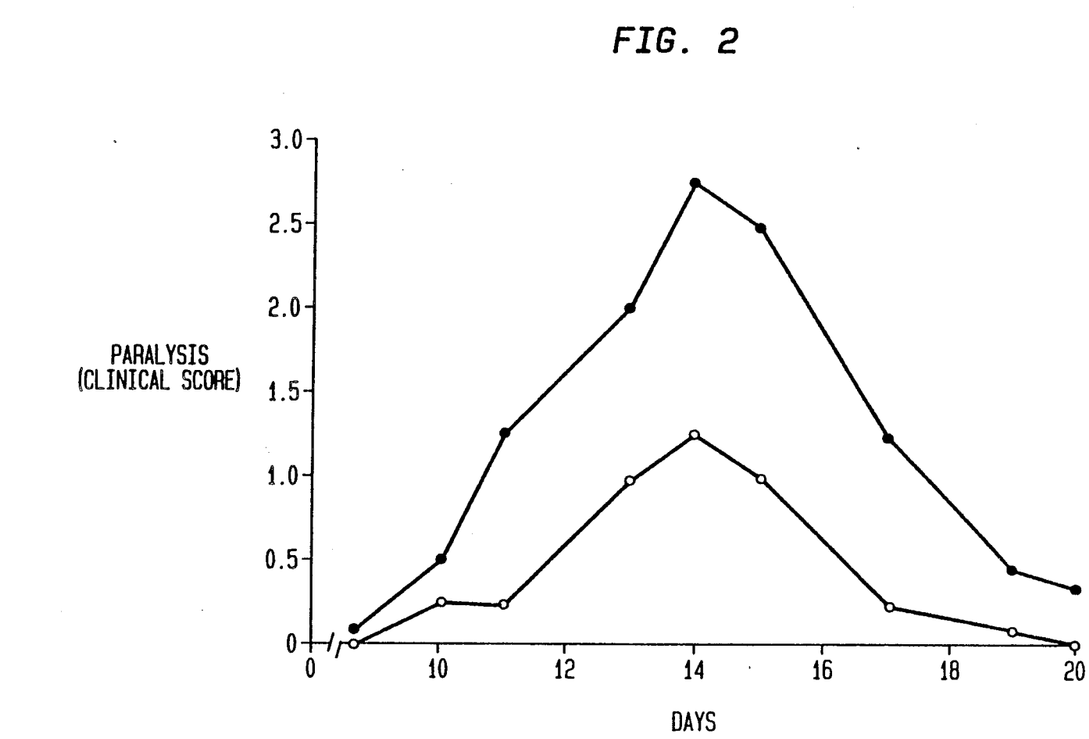

FIG. 2 shows the results of an experiment in which rats were administered two doses each of 0.05 micrograms of a membrane fraction of Z1a line cells at weekly intervals, and two weeks later active EAE was induced in the rats. It can be seen that the rats treated with the membrane fraction suffered very mild paralysis compared to the control rats. Thus, the course of the disease could be, markedly alleviated using specific membrane fractions. Table IV shows the results of vaccinating rats with pressure activated anti-BP line cells. It can be seen that rats treated with control line cells were susceptible to EAE while rats treated with pressure activated, specific anti-BP line cells were completely resistant to active EAE. They were also resistant to EAE mediated by intact, anti-BP line cells (not shown). See also Table VI for results of pressure-treated, cross-linking agent treated membrane preparations used as a vaccine against AA.

Examples of autoimmune diseases that can be treated using membrane protein of autoimmune line cells:

| Human autoimmune diseases | Antigen used to activate T lymphocytes |
| --- | --- |
| Multiple sclerosis | (a) Myelin basic protein |
|  | (b) Crude extract of central nervous system |
| Thyroiditis | (a) Thyroglobulin |
|  | (b) Crude extract of thyroid gland |
| Diabetes (Type I) | (a) Extract of Islet cells |
| Ankylosing spondylitis (specific types) | (a) Certain Klebsiella bacteria |
|  | (b) Crude extract of joints |
| Rheumatoid arthritis | (a) Crude extract of joints |

EXAMPLE: PREPARATION OF VACCINE

Cells from a line of T lymphocytes directed against the myelin basic protein were used (Z1a line). These cells induce experimental autoimmune encephalitis (EAE) in rats $6 \times 10^8$ cells, suspended in 2.5 ml of phosphate buffered saline pH 7.2 (PBS), were placed in a sterile pressure chamber. The lid was placed directly on top of the solution to eliminate any air bubbles. Pressure was applied gradually by a French Press (15 min) to reach 1000 atmospheres and maintained at this pressure for 45 min. The pressure was then slowly reduced (15 min) to atmospheric pressure. The cells were transferred to a test tube, spun down at 1500 rpm and the precipitate was separated. Cell viability, tested by trypan blue exclusion, was over 90%. The supernatant was then ultracentrifuged at 100,000 g for one hour. The supernatant (about 600 micrograms proteins in 2 ml PBS) was collected and used in the in vitro and in vivo functional experiments described below.

In the in vitro experiment, cells of the Z1a line induced to proliferate by the addition of their specific antigen (0.2 micrograms/ml myelin basic protein).

Cell proliferation was expressed by counts per minute of incorporated radioactive thymidine. The addition of 30 micrograms/ml of the shed proteins (see above) resulted in reduction of cell proliferation by 40-60%. When 30 micrograms/ml of proteins shed from other T line cells (including arthritis) were used, no effect on cell proliferation was observed. Typical results of such an experiment are shown in table III, and indicate that the material shed from the cell surface pressure includes a specific receptor to the inducing antigen.

This material may be used for immunization against the receptor resulting in partial or complete elimination of the autoimmune disease. Such an experiment is described below.

Rats were first preimmunized twice at a week's interval by inoculation of 0.5 micrograms soluble proteins shed by pressure of the Z1a line cells. Two weeks later the rats were challenged with BP antigen in adjuvant. After 14 days all rats in the control group manifested severe EAE while the pretreated rats showed only a mild form of EAE. Typical profiles after challenge with an encephalitogenic dose of BP are shown in FIG. 2. Again, pretreatment of rats with proteins shed by pressure of an unrelated line (arthritis) showed no effect on the development of EAE.

TABLE IV

Vaccination against EAE using pressure-treated, activated anti-BP line cells

| Treatment of rats with pressure-treated activated line cell | EAE induced by active immunization with BP/CFA | |
|---|---|---|
| | Incidence | Clinical severity |
| Control | 30/30 | moderate to severe |
| Anti-BP | 5/30 | none to very mild |

Lewis rats were inoculated intraperitoneally with anti-BP or control line cells (5 × $10^6$ weekly × 4) that had been activated and treated with hydrostatic pressure (1150 atm. for 15 min.) and challenged 1 week later with BP/CFA to induce active EAE.

TABLE V

Vaccination against experimental autoimmune thyroiditis using T lymphocyte vaccines

| T Lymphocyte Vaccine | Treatment of T lymphocytes | Percent Indicidence of Thyroiditis |
|---|---|---|
| None | None | 100 |
| Anti-Tg | Pressure | 45 |
| Anti-Tg | Colchicine + cytochalasin | 59 |
| Anti-Tg | Formaldehyde | 35 |

Groups of 10 mice each of strain C3H/eBxC57BL/6J)F1 were induced to develop experimental autoimmune thyroiditis by an intravenous inoculation of 2 × $10^6$ anti-thyroglobulin (anti-Tg) line T lymphocytes. Before induction of disease, some mice were treated with 3 weekly subcutaneous injections of 10 × $10^6$ activated anti-Tg line T cells that had been treated with pressure, colchicine plus cytochalasin, or formaldehyde, as described in the legend to FIG. 3. The severity of thyroiditis was graded by histological examination of the thyroid glands 1 week later.

TABLE I

Experimental Autoimmune Diseases Actively Induced, or Produced by Autoimmune T Lymphocyte Line Cells

| | | | Actively induced disease | | | | Disease produced by line cells | | | |
|---|---|---|---|---|---|---|---|---|---|---|
| Disease | Species | Target Organ | Self-Antigen | Immunization | Latency (days) | Course | Antigen for line selection | Cell inoculum | Recipients | Latency (days) | Course |
| EAE* | Rat | White matter of CNS | BP | BP/CFA | 12 | Acute | BP | $10^4$–$10^5$ | Intact | 3–6 | Acute |
| EAT | Mouse | Thyroid | Tg | Tg/CFA | 30 | Chronic | Tg | $10^4$–$10^5$ | Intact | 1–3 | Chronic |
| AA | Rat | Joints | ? | CFA | 14 | Subacute | Tb | $10^7$ | Irradiated | 5–10 | Subacute |

*Abbreviations used in Tables:
AA, adjuvant arthritis; BP, myelin basic protein; CFA, complete Freund's adjuvant; CNS, central nervous system; EAE, experimental autoimmune encephalomyelitis; EAT, experimental autoimmune thyroiditis; IFA, incomplete Freund's adjuvant; Tb, Mycobacterium tuberculosis organisms; Tg, thyroglobulin.

TABLE II

Vaccination Against Autoimmune Diseases Using Specific Autoimmune Line Cells

| | Vaccine | | Resistance to Disease | | |
|---|---|---|---|---|---|
| Disease | Line cells | Treatment | Activity induced | Line mediated | Degree of resistance |
| EAE | anti-BP | Irradiation | yes | no | 60–70% |
| EAT | anti-Tg | Irradiation | yes | yes | incomplete autoantibodies develop |
| AA | anti-Tb | none | yes | ? | complete complete |

Rats or mice inoculated intravenously with activated line cells (anti-BP, 5 × $10^6$; anti-Tg, 5 × $10^6$; anti-Tb, 2 × $10^7$), some of which had been treated by irradiation (1,500 R). Control animals (not shown) were inoculated with line cells directed against irrelevant antigens. Two to four weeks later, the animals were challenged to induce active autoimmune diseases.

TABLE III

Membrane fractions inhibit proliferative responses of specific line cells

| | Proliferative response to sepcific antigen % inhibition of line | |
|---|---|---|
| Cellular orgin of membrane fraction | A2 | Z1a |
| A2 | 39 | 0 |
| A1a | 0 | 50 |

Membrane fractions from the A2 (arthritis) and the Z1a (encephalomelitis) cell lines were obtained using the pressure method (1,000 atm) and 50 micrograms/ml were included in the proliferative responses to specific antigen of the intact line cells. The % inhibition was computed by comparing the response in the presence of the membrane fraction obtained from the specific line cells to the response in the presence of the membrane fraction obtained from the specific line cells to the response in the presence of the membrane fraction for the other line cells. Experiments carried out with pressure-treated, activated cells gave practically identical results.

TABLE VI

Vaccination against AA using isolated membrane preparations of pressurized and cross-linked T lymphocytes

| Vaccination with | | Induction of AA by MT | |
|---|---|---|---|
| A2b clone membranes | | Incidence | Mean AA score |
| Pressure | Formaldehyde | of AA | on day 20 |
| None | None | 100 | 53 |
| Yes | None | 100 | 55 |
| Yes | Yes | 50 | 15 |

Groups of 10 Lewis rats were or were not vaccinated subcutaneously 4 times at weekly intervals with 1.2 mg of A2b isolated membrane preparations. One week later the rats were challenged with MT (1 mg in oil) to induce AA. The clinical score on day 20 of affected rats is recorded at a scale of 0 to 100% as described in the legend to FIG. 3.

Isolated membranes were prepared as follows: 3 × $10^8$ activated A2b T cells were treated with hydrostatic pressure (1500 bars for 15 min.) and one half of the cells were also treated with the cross-linker formaldehyde (0.3%, 15 min.) and washed six times in PBS. Membranes were obtained by lysing the cells in a hypotonic solution of NaCl (½ physiological osmolarity + PMSF ($10^{-5}$ M) + azide (0.02%). The cells were homogenized in a polytron homogenizer (6.5 min., 2.5 units for 30 seconds at 4° C.) and the membranes isolated with a 41% sucrose gradient (96,000 g, 2 h, Rotter SW28, at 4° C.). The membranes were dialyzed against PBS (2 h, 4° C.) and proteins were measured by Bradford analysis: The yield of membrane protein was 1.5–2 mg.

REFERENCES

1. Ben-Nun, A., Wekerle, H. and Cohen, I. R. (1981). Eur. J. Immun. 11: 195–199.

2. Ben-Nun, A. and Cohen, I. R. (1982). J. Immunol. 128:1450–1457.
3. Ben-Nun, A. and Cohen, I. R. (1982). J. Immunol. 129:303–308.
4. Ben-Nun, A., Eisenstein, S. and Cohen, I. R. (1982). J. Immunol. 129:918.
5. Holoshitz, J., Naparstek, Y., Ben-Nun, A., and Cohen, I. R. (1983). Science 219:56–58.
6. Ben-Nun, A., Wekerle, H. and Cohen, I. R. (1981). Nature 292:60–61.
7. Ben-Nun, A. and Cohen, I. R. (1981). Eur. J. Immunol. 11:949–952.
8. Maron, R., Zeubavel, R., Friedman, A. and Cohen, I. R. (1983). J. Immunol. 131:2316–2320.
9. Holoshitz, J., Frenkel. A., Ben-Nun, A. and Cohen, I. R. (1983). J. Immunol. 131:2810–2813.
10. Paterson, P. Y. (1976) In: *Textbook of Immunopathology*. (Meischer, P. and Muller-Eberhard, H. J. Eds) 2nd Ed., pp. 179–213. Grune & Stratton, N.Y.
11. Rose, N. R., Twarog, F. J. and Crowle, A. J. (1971). J. Immunol. 106:698–708.
12. Pearson, C. M. (1963). J. Chronic Dis. 16:863–874.
13. Trentham, D. E. McCunr, W. J. Susman, P. and David, J. R. (1980). J. Clin. Invest. 66:1109–1117.
14. Iizuka, Y. and Chang, Y. H. (1982). Arthritic Rheum. 25:1325–1332.
15. Holoshitz, J., Matitiau, A. and Cohen, I. R. (1984). J. Clin. Invest. 73:211–215.
16. Duskin, et al., (1985). Cell 5:83–86.
17. Trentham D. E., et al. (1977). J. Exp. Med. 146:857.
18. Pearson, C. M. (1956). Proc. Soc. Exp. Bio. Med. 91:95.
9. Holoshitz, J., et al., (1983). Science 219-56.
20. Lieder, O., et al., (1986). Ann. N.Y. Acad. Sci. 475: 267.

What is claimed is:

1. A preparation for preventing or treating an autoimmune disease, comprising T-lymphocyte cells which have developed specificity for the autoimmune disease specific antigen and which cells have been activated either by incubating in the presence of the autoimmune disease specific antigen or by incubating with a mitogen capable of inducing an immune response by the T-lymphocyte cells, following which said cells have been pressure treated by means of hydrostatic pressure of sufficient pressure and time to cause augmented antigenicity of the T-lymphocyte cells without substantial loss of membrane proteins from the cells.

2. A preparation in accordance with claim 1, wherein the specific autoimmune disease is multiple sclerosis, thyroiditis, diabetes type I, ankylosing spondylitis, rheumatoid arthritis, or myasthenia gravis.

3. A preparation in accordance with claim 1, which cells have additionally been chemically cross-linked by treatment with a chemical cross-linking agent.

4. A preparation in accordance with claim 3, wherein said cells have been chemically cross-linked by treatment with said chemical cross-linking agent after being treated with pressure.

5. A preparation in accordance with claim 3, wherein said cells have been chemically cross-linked by treatment with said chemical cross-linking agent prior to being treated with pressure.

6. A preparation in accordance with claim 1, wherein said cells have additionally had their cytoskeletons dissociated treatment with a cytoskeletal disrupting agent prior to being treated with pressure.

7. A preparation in accordance with claim 6, wherein said cells have additionally been chemically cross-linked by treatment with a chemical cross-linking agent.

8. A preparation for preventing or treating an autoimmune disease, comprising T-lymphocyte cells which have developed specificity for the autoimmune disease specific antigen and which cells have been activated either by incubating in the presence of the autoimmune disease specific antigen or by incubating with a mitogen capable of inducing an immune response by the T-lymphocyte cells, following which said cells have been chemically cross-linked by treatment with a chemical cross-linking agent.

9. A preparation in accordance with claim 8, wherein the specific autoimmune disease is multiple sclerosis, thyroiditis, diabetes type I, ankylosing spondylitis, rheumatoid arthritis, or myasthenia gravis.

10. A preparation in accordance with claim 9, wherein said chemical cross-linking agent is formaldehyde or glutaraldehyde.

11. A preparation comprising fixed cell membranes recovered from lysed treated T-lymphocyte cells of the preparation in accordance with claim 8.

12. A preparation for preventing or treating an autoimmune disease, comprising T-lymphocyte cells which have developed specificity for the autoimmune disease specific antigen and which cells have been activated either by incubating in the presence of the autoimmune disease specific antigen or by incubating with a mitogen capable of inducing an immune response by the T-lymphocyte cells, following which said cells have had their cytoskeletons dissociated by treatment with a cytoskeletal disrupting agent.

13. A preparation in accordance with claim 12, wherein the specific autoimmune disease is multiple sclerosis, thyroiditis, diabetes type I, ankylosing spondylitis, rheumatoid arthritis, or myasthenia gravis.

14. A preparation in accordance with claim 12, wherein said cells have additionally been chemically cross-linked by treatment with a chemical cross-linking agent.

15. A preparation in accordance with claim 12, wherein said cytoskeletal disrupting agent is cytochalsin or colchicine.

16. A preparation comprising fixed cell membranes recovered from lysed treated T-lymphocyte cells of the preparation in accordance with claim 14.

17. A method for producing treated T-lymphocyte cells useful for preventing or treating a specific autoimmune disease, comprising the steps of:
(a) activating T-lymphocyte cells, which cells have developed specificity for the autoimmune disease specific antigen, either by incubating in the presence of the autoimmune disease specific antigen or by incubating with a mitogen capable of inducing an immune response by the T-lymphocyte cells;
(b) suspending said activated T-lymphocyte cells in a buffer; and
(c) subjecting said suspended cells to a hydrostatic pressure of sufficient pressure and time to cause augmented antigenicity of said T-lymphocyte cells without substantial loss of membrane proteins from said T-lymphocyte cells.

18. A method in accordance with claim 17, wherein said T-lymphocyte cells are subjected to a pressure of from 500 to about 1500 atmospheres.

19. A method in accordance with claim 17, further including the step of, prior to said step (c), chemically cross-linking said activated T-lymphocyte cells by treatment with a chemical cross-linking agent.

20. A method in accordance with claim 19, further including the step of, prior to step (c) dissociating the cytoskeletons of said activated T-lymphocyte cells by treatment with a cytoskeletal disrupting agent.

21. A method in accordance with claim 17, further including the step of, subsequent to step (c), chemically cross-linking said activated T-lymphocyte cells by treatment with a chemical cross-linking agent.

22. A method in accordance with claim 17, further including the step of, prior to step (c), dissociating the cytoskeletons of said activated T-lymphocyte cells by treatment with a cytoskeletal disrupting agent.

23. A method for producing treated T-lymphocyte cells useful for preventing or treating a specific autoimmune disease, comprising the steps of:
   (a) activating T-lymphocyte cells, which cells have developed specificity for the autoimmune disease specific antigen either by incubating in the presence of the autoimmune disease specific antigen or by incubating with a mitogen capable of inducing an immune response by the T-lymphocyte cells;
   (b) suspending said activated T-lymphocyte cells in a buffer; and
   (c) chemically cross-linking said suspended cells by subjecting said suspended cells to a chemical cross-linking agent.

24. A method for producing treated T-lymphocyte cells useful for preventing or treating a specific autoimmune disease, comprising steps of:
   (a) activating T-lymphocyte cells, which cells have developed specificity for the autoimmune disease specific antigen, either by incubating in the presence of the autoimmune disease specific antigen or by incubating with a mitogen capable of inducing an immune response by the T-lymphocyte cells;
   (b) suspending said activated T-lymphocyte cells in a buffer; and
   (c) dissociating the cytoskeletons of said suspended cells by subjecting said suspended cells to a cytoskeletal disrupting agent.

25. A method in accordance with claim 24, further including the step of, subsequent to step (c), chemically cross-linking said activated T-lymphocyte cells having dissociated cytoskeletons by treatment with a chemical cross-linking agent.

26. A composition for preventing or treating a specific autoimmune disease, comprising a preparation in accordance with claim 1 and a pharmaceutically acceptable carrier.

27. A composition for preventing or treating a specific autoimmune disease, comprising a preparation in accordance with claim 8 and a pharmaceutically acceptable carrier.

28. A composition for preventing or treating a specific autoimmune disease, comprising a preparation in accordance with claim 12 and a pharmaceutically acceptable carrier.

29. A method for recovering purified membrane proteins useful for preventing or treating a specific autoimmune disease, comprising:
   (a) activating T-lymphocyte cells, which cells have developed specificity for the autoimmune disease specific antigen, either by incubating in the presence of the autoimmune disease specific antigen or by incubating with a mitogen capable of inducing an immune response by the T-lymphocyte cells;
   (b) suspending said activated T-lymphocyte cells in a buffer;
   (c) either subjecting said suspended cells to a hydrostatic pressure of sufficient pressure and time to cause shedding of membrane proteins therefrom and then chemically cross-linking said pressure-treated suspended cells by subjecting said suspended cells to a chemical cross-linking agent, or chemically cross-linking said suspended cells by subjecting said suspended cells to a chemical cross-linking agent and then subjecting said cross-linked suspended cells to a hydrostatic pressure of sufficient pressure and time to cause shedding of membrane proteins therefrom; and
   (d) recovering said shed proteins.

30. A method in accordance with claim 29, further including the step of, prior or subsequent to said pressure-treatment step, dissociating the cytoskeletons of said T-lymphocyte cells by treatment with a cytoskeletal disrupting agent.

31. A method for recovering purified membrane proteins useful for preventing or treating a specific autoimmune disease, comprising:
   (a) activating T-lymphocyte cells, which cells have developed specificity for the autoimmune disease specific antigen, either by incubating in the presence of the autoimmune disease specific antigen or by incubating with a mitogen capable of inducing an immune response by the T-lymphocyte cells;
   (b) suspending said activated T-lymphocyte cells in a buffer;
   (c) dissociating the cytoskeletons of said suspended cells by subjecting said suspended cells to a cytoskeletal disrupting agent;
   (d) subjecting said suspended cells with dissociated cytoskeletons to a hydrostatic pressure of sufficient pressure and time to cause shedding of membrane proteins therefrom; and
   (e) recovering said shed proteins.

32. A preparation for preventing or treating an autoimmune disease, comprising membrane proteins shed from T-lymphocyte cells which had developed specificity for the autoimmune disease specific antigen and which cells had been activated either by incubating in the presence of the autoimmune disease specific antigen or by incubating with a mitogen capable of inducing an immune response by the T-lymphocyte cells, wherein said proteins are those recovered from the hydrostatic pressure treatment of said activated T-lymphocyte cells at a pressure and for a time sufficient to cause shedding of membrane proteins therefrom, and wherein said shed proteins have been chemically cross-linked by treatment with a chemical cross-linking agent either before or after the pressure treatment.

33. A preparation in accordance with claim 32, wherein said shed proteins have further had their cytoskeletons dissociated by treatment with a cytoskeletal disrupting agent before the pressure treatment.

34. A preparation for preventing or treating an autoimmune disease, comprising membrane proteins shed from T-lymphocyte cells which had developed specificity for the autoimmune disease specific antigen and which cells had been activated either by incubating in the presence of the autoimmune disease specific antigen or by incubating with a mitogen capable of inducing an immune response by the T-lymphocyte cells, wherein said proteins are those recovered from the hydrostatic pressure treatment of said activated T-lymphocyte cells at a pressure and for a time sufficient to cause shedding of membrane proteins therefrom, which activated T-lymphocyte cells, prior to said pressure treatment, had had their cytoskeletons dissociated by treatment with a cytoskeletal disrupting agent.

* * * * *